United States Patent
Lee et al.

(10) Patent No.: US 12,016,726 B2
(45) Date of Patent: Jun. 25, 2024

(54) FLEXIBLE ULTRASOUND TRANSDUCER AND METHOD FOR MANUFACTURING THE SAME

(71) Applicant: KOREA INSTITUTE OF SCIENCE AND TECHNOLOGY, Seoul (KR)

(72) Inventors: Byung Chul Lee, Seoul (KR); Shinyong Shim, Seoul (KR); Dong-Hyun Kang, Seoul (KR); Hae Youn Kim, Seoul (KR); Hyung Min Kim, Seoul (KR); Ki Joo Pahk, Seoul (KR); Maesoon Im, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 6 days.

(21) Appl. No.: 17/326,335

(22) Filed: May 21, 2021

(65) Prior Publication Data
US 2022/0047245 A1 Feb. 17, 2022

(30) Foreign Application Priority Data
Aug. 13, 2020 (KR) ........................ 10-2020-0101870

(51) Int. Cl.
*A61B 8/00* (2006.01)
*A61N 7/00* (2006.01)
(Continued)

(52) U.S. Cl.
CPC .......... *A61B 8/4494* (2013.01); *A61B 8/4488* (2013.01); *A61N 7/00* (2013.01);
(Continued)

(58) Field of Classification Search
CPC ... A61B 8/4494; A61B 8/4488; A61B 8/4483; A61B 2090/378; A61B 2018/00577;
(Continued)

(56) References Cited

U.S. PATENT DOCUMENTS

| 8,974,393 B2 | 3/2015 | Cho et al. |
| 9,392,992 B2 | 7/2016 | Hsu et al. |

(Continued)

FOREIGN PATENT DOCUMENTS

| CN | 101558552 A | 10/2009 |
| CN | 103221093 A | 7/2013 |

(Continued)

OTHER PUBLICATIONS

International Search Report; International Application No. 202110644184.5; International Filing Date: Aug. 13, 2020; dated Dec. 22, 2023; 5pages.

*Primary Examiner* — Colin T. Sakamoto
*Assistant Examiner* — Tommy T Ly
(74) *Attorney, Agent, or Firm* — CANTOR COLBURN LLP

(57) ABSTRACT

A flexible ultrasound transducer according to an embodiment of the present disclosure includes a substrate having a central part and a plurality of extended parts extending from the central part; an ultrasound probe disposed at the central part of the substrate to acquire an ultrasound image of a region of interest; and a focused ultrasound output unit disposed at the extended parts of the substrate to output a focused ultrasound to the region of interest, wherein the focused ultrasound output unit disposed at the extended parts of the substrate has a flexible property and is deformable. According to the structure of an embodiment, it is possible to simultaneously achieve ultrasound imaging and ultrasonic therapy such as lesion stimulation or removal through focused ultrasound, and adjust the focal position of focused ultrasound or improve the focal sensitivity through flexible movement.

4 Claims, 10 Drawing Sheets

(51) Int. Cl.
*B06B 1/02* (2006.01)
*G01S 7/52* (2006.01)
*G01S 15/89* (2006.01)

(52) U.S. Cl.
CPC ........ B06B 1/0292 (2013.01); G01S 7/52079 (2013.01); G01S 15/8915 (2013.01); *A61N 2007/0052* (2013.01); *B06B 2201/76* (2013.01)

(58) Field of Classification Search
CPC ............... A61B 8/4477; A61N 7/00; A61N 2007/0052; A61N 7/02; A61N 2007/0078; B06B 1/0292
See application file for complete search history.

(56) References Cited

U.S. PATENT DOCUMENTS

| | | | |
|---|---|---|---|
| 2007/0013269 A1* | 1/2007 | Huang | H02N 1/006 |
| | | | 310/334 |
| 2010/0069754 A1* | 3/2010 | Raju | A61B 8/0808 |
| | | | 600/439 |
| 2010/0280388 A1 | 11/2010 | Huang | |
| 2013/0176816 A1* | 7/2013 | Nakamura | G10K 11/32 |
| | | | 310/334 |
| 2014/0005521 A1* | 1/2014 | Kohler | A61B 6/4057 |
| | | | 601/3 |
| 2019/0038253 A1 | 2/2019 | Song et al. | |
| 2019/0142380 A1* | 5/2019 | Emery | A61N 7/02 |
| | | | 600/439 |
| 2019/0366126 A1 | 12/2019 | Pahk et al. | |
| 2021/0128107 A1* | 5/2021 | Hakkens | G01S 15/8906 |
| 2022/0218308 A1 | 7/2022 | Oh | |

FOREIGN PATENT DOCUMENTS

| | | | | |
|---|---|---|---|---|
| CN | 109589132 A | | 4/2019 | |
| EP | 2977113 A1 | * | 1/2016 | .......... B06B 1/0292 |
| KR | 10-1330733 B1 | | 11/2013 | |
| KR | 10-2014-0027811 A | | 3/2014 | |
| KR | 10-2017-0058631 A | | 5/2017 | |
| KR | 10-2019-0004701 A | | 1/2019 | |
| KR | 10-1935375 B1 | | 1/2019 | |
| KR | 10-2020-0056895 A | | 5/2020 | |
| KR | 20200056895 A | * | 5/2020 | .............. A61N 7/00 |
| KR | 10-2124422 B1 | | 6/2020 | |
| KR | 10-2020-0097750 A | | 8/2020 | |
| WO | 2006134580 A2 | | 12/2006 | |
| WO | 2012066477 A1 | | 5/2012 | |
| WO | 2017/182655 A1 | | 10/2017 | |
| WO | 2019/110133 A1 | | 6/2019 | |
| WO | 2020007753 A1 | | 1/2020 | |

* cited by examiner

Trench structure

FLEXIBLE ULTRASOUND TRANSDUCER AND METHOD FOR MANUFACTURING THE SAME

CROSS-REFERENCE TO RELATED APPLICATION

This application claims priority to Korean Patent Application No. 10-2020-0101870, filed on Aug. 13, 2020, and all the benefits accruing therefrom under 35 U.S.C. § 119, the contents of which in its entirety are herein incorporated by reference.

BACKGROUND

Field

The present disclosure relates to an ultrasound transducer and a method for manufacturing the same, and more particularly, to a dual mode ultrasound transducer including an ultrasound probe disposed at the central part of a substrate and a focused ultrasound output unit disposed at an extended part of the substrate having a flexible property, thereby simultaneously achieving ultrasound image acquisition and focused ultrasound treatment, and a method for manufacturing the same.

DESCRIPTION OF GOVERNMENT-FUNDED RESEARCH AND DEVELOPMENT

This research is conducted by Korea Institute of Science and Technology under the support of biotechnology and medical technology development project (Development of ultrasound probes and attachable devices using semiconductor technology, Project Series No. 1711093060, 1711105874) of the Ministry of Science and ICT.

DESCRIPTION OF THE RELATED ART

An ultrasound probe includes an array of ultrasound transducers, and each ultrasound transducer simultaneously plays the role of a transmitter to output an ultrasound beam to a region of interest and a receiver to receive the ultrasound beam reflecting from an object in the region of interest. The travel time of the ultrasound may be measured by calculating the transmission time and the receipt time of the ultrasound beam, and using this, image information of the object in the region of interest may be generated. The generated ultrasound image information may be visualized through a display. The ultrasound probe can image the inner part of the body in a noninvasive manner and thus is widely in the medical field.

Meanwhile, to conduct therapy for a patients pain relief or stimulation of a nerve cell of a specific body part, insertion of electrodes into the patients body has been used, but there is the risk of damage to the human body by the mechanical invasive process. Recently, ultrasound stimulation therapy that stimulates an affected part without a mechanical invasive process is widely used. Ultrasound may be classified into High-intensity Focused Ultrasound (HIFU) and Low-intensity Focused Ultrasound (LIFU) according to the intensity, and it is known that HIFU is used in direct treatment for mechanically removing living tissues such as cancer cells, tumors and lesions, while LIFU has a medical effect without necrotizing human body tissues. For example, it is possible to treat neurological disorders including cognitive impairment, anxiety and depression using LIFU in a noninvasive manner, or remove lesions using HIFU in a noninvasive manner.

However, the existing focused ultrasound based therapy does not use the process of removing a lesion immediately after locating the lesion in real time, and medical personnel performs surgery while seeing an image of the inner part of patients body acquired through CT or MRI, resulting in low accuracy, and since it is not easy to accurately identify the boundaries between the lesion and the surrounding tissues, there is the risk of damage to functionally important tissues that do not need to cut.

SUMMARY

The present disclosure is directed to providing a dual mode flexible ultrasound transducer for simultaneously achieving ultrasound image acquisition and treatment through focused ultrasound, and controlling the focal position or improving the focal sensitivity through flexible movement, and a method for manufacturing the same.

A flexible ultrasound transducer according to an embodiment includes a substrate having a central part and a plurality of extended parts extending from the central part; an ultrasound probe disposed at the central part of the substrate to acquire an ultrasound image of a region of interest; and a plurality of focused ultrasound output units disposed at the plurality of extended parts of the substrate to output a focused ultrasound to the region of interest, wherein the extended parts of the substrate and the focused ultrasound output units are flexible and deformable.

According to an embodiment, the ultrasound probe may include an array of imaging ultrasound output elements configured to output an imaging ultrasound toward the region of interest.

According to an embodiment, the ultrasound probe may include a one-dimensional array in which the plurality of imaging ultrasound output elements is linearly arranged or a two-dimensional array in which the plurality of ultrasound output elements is arranged in a surface.

According to an embodiment, the focused ultrasound output unit may include an array of focused ultrasound output elements configured to output a focused ultrasound for treatment to the region of interest.

According to an embodiment, the extended parts of the substrate may have a plurality of trench structures formed at a predetermined interval, and the focused ultrasound output unit may include a flexible material layer that covers the plurality of trench structures and the array of focused ultrasound output elements.

According to an embodiment, the focused ultrasound output unit may further include a reinforcing layer made of a material having a larger thermal expansion coefficient than the flexible material layer below the extended parts of the substrate.

According to an embodiment, the focused ultrasound for treatment may be Low-intensity Focused Ultrasound (LIFU) for stimulating the region of interest with low intensity or High-intensity Focused Ultrasound (HIFU) for mechanically removing a lesion in the region of interest.

According to an embodiment, the imaging ultrasound output elements and the focused ultrasound output elements may be a micromachined ultrasound transducer (MUT).

A method for manufacturing a flexible ultrasound transducer according to an embodiment includes providing a substrate; arranging a plurality of focused ultrasound output elements on the substrate at a predetermined interval; forming a photoresist on the plurality of focused ultrasound output elements; forming a plurality of trench structure between the plurality of focused ultrasound output elements by etching the substrate; and forming a flexible material layer that covers the plurality of trench structures and the plurality of focused ultrasound output elements.

According to an embodiment, the ultrasound output element may be a micromachined ultrasound transducer.

According to an embodiment, the flexible material layer may be made of elastomer including at least one of polydimethylsiloxane (PDMS), polyurethane, polyester or a mixture thereof.

According to an embodiment, the method for manufacturing a flexible ultrasound transducer may further include forming a reinforcing layer made of a material having a larger thermal expansion coefficient than the flexible material layer below the substrate.

According to an embodiment, the method for manufacturing a flexible ultrasound transducer may further include applying heat to the flexible material layer and the reinforcing layer to bend the flexible ultrasound transducer.

According to an embodiment of the present disclosure, there is provided a flexible ultrasound transducer designed to simultaneously achieve ultrasound imaging and ultrasonic therapy (for example, stimulation or removal of lesions using Low-intensity Focused Ultrasound (LIFU) or High-intensity Focused Ultrasound (HIFU)), and adjust the focal position of focused ultrasound as desired by users through flexible movement or improve the focal sensitivity necessary for ultrasound imaging and treatment.

DETAILED DESCRIPTION

Figure 1:
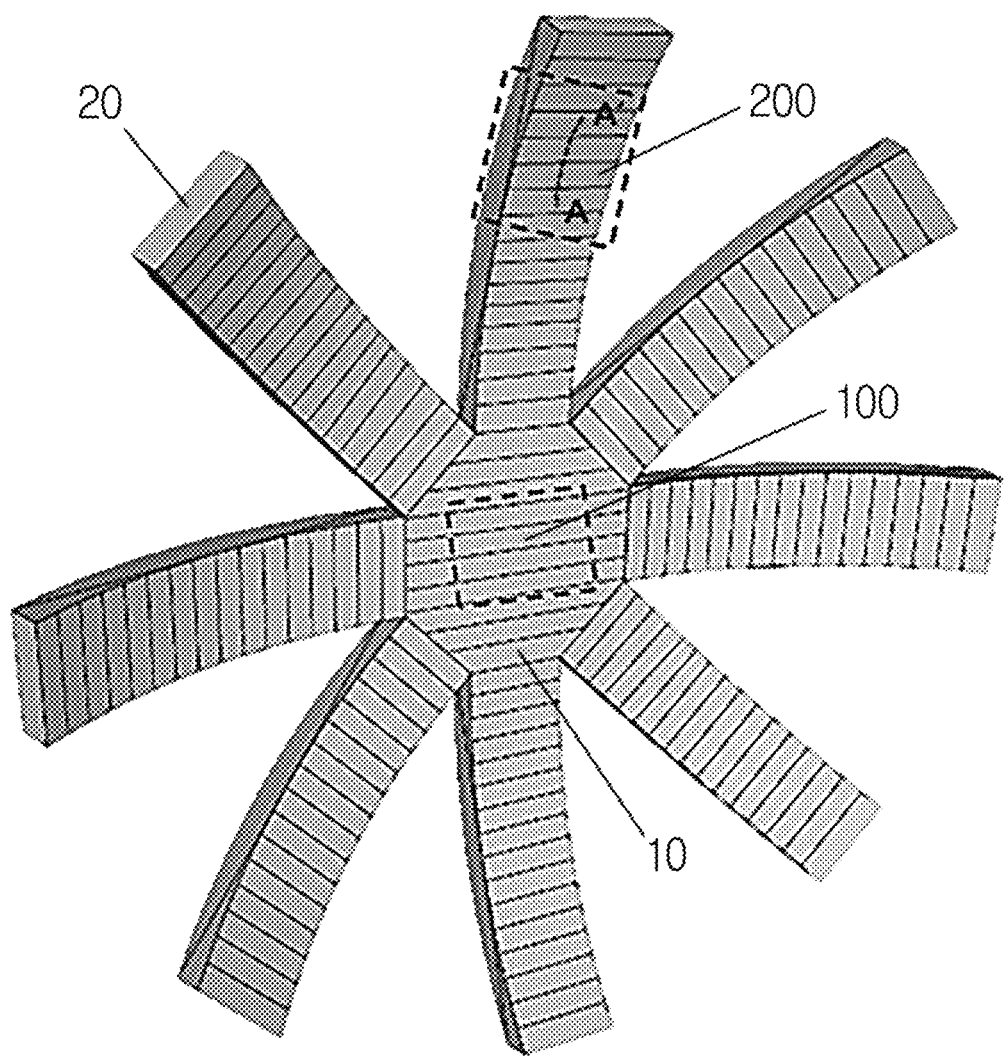
FIG. 1 shows the structure of a flexible ultrasound transducer according to an embodiment.

The following detailed description of the present disclosure is made with reference to the accompanying drawings, in which particular embodiments for practicing the present disclosure are shown for illustration purposes. These embodiments are described in sufficiently detail for those skilled in the art to practice the present disclosure. It should be understood that various embodiments of the present disclosure are different but do not need to be mutually exclusive. For example, particular shapes, structures and features described herein in connection with one embodiment may be embodied in other embodiment without departing from the spirit and scope of the present disclosure. It should be further understood that changes may be made to the positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

Hereinafter, the embodiments will be described in detail with reference to the accompanying drawings, but the claimed scope is not restricted or limited by the embodiments.

FIG. 1 shows the structure of a flexible ultrasound transducer according to an embodiment.

Referring to FIG. 1, the flexible ultrasound transducer according to an embodiment includes a substrate having a central part 10 and a plurality of extended parts 20 extending from the central part 10, an ultrasound probe 100 disposed at the central part 10 of the substrate to acquire an ultrasound image of a region of interest, and a focused ultrasound output unit 200 disposed at the extended part 20 of the substrate to output a focused ultrasound to the region of interest. The focused ultrasound output unit 200 disposed at the extended part 20 has a flexible property and elasticity, and is prone to deform and recover.

Figure 2:
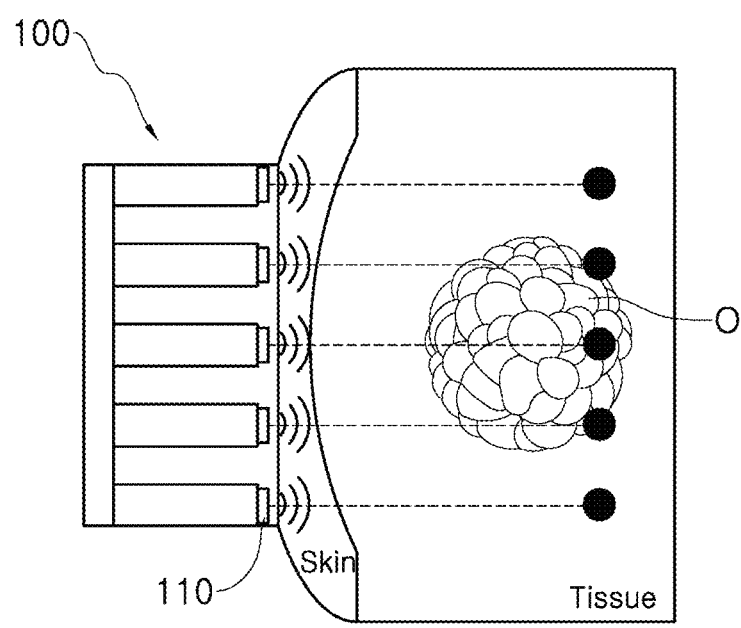
FIG. 2 shows the lesion detection using an ultrasound probe disposed at a central part of a substrate of a flexible ultrasound transducer according to an embodiment.

FIG. 2 shows the lesion detection using the ultrasound probe 100 disposed at the central part of the substrate of the flexible ultrasound transducer according to an embodiment.

Referring to FIG. 2, the ultrasound probe 100 includes an array of imaging ultrasound output elements 110. Each imaging ultrasound output element 110 outputs an ultrasound toward the region of interest, and the output ultrasound beam reflects back to the ultrasound probe 100 from an object (for example, a lesion, a tumor, an organ, etc.) disposed on the travel path. The ultrasound probe 100 detects the location or shape of the object based on the travel time information of the ultrasound. A processing device connected to the ultrasound probe 100 may acquire location and shape information of the object in real time and visualize it through a display. In this way, lesion detection is performed using the ultrasound probe at the central part of the substrate.

The ultrasound probe 100 shown in FIGS. 1 and 2 has a one-dimensional (1D) array structure in which the plurality of imaging ultrasound output elements is linearly arranged side by side. According to an embodiment, the ultrasound probe of one-dimensional array structure may acquire a two-dimensional (2D) image (a flat image) of the region of interest by 360° rotation simultaneously with imaging.

Figure 3A:
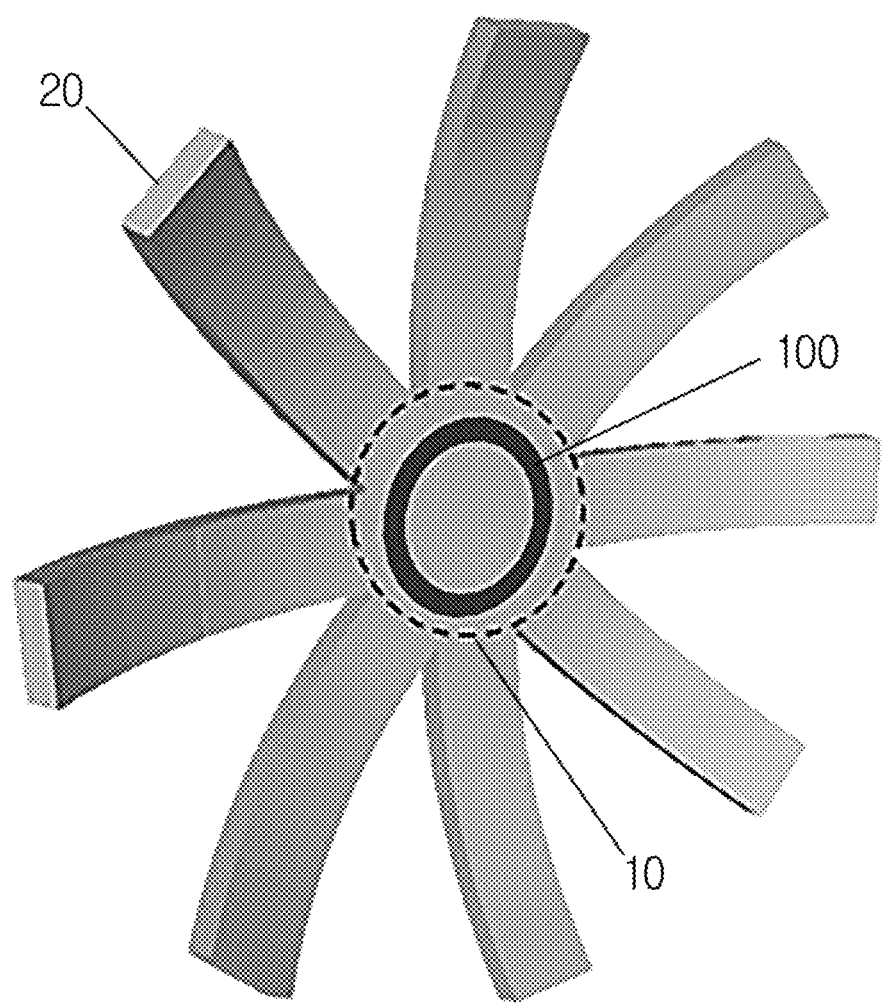
FIGS. 3A and 3B show the structure of a flexible ultrasound transducer according to another embodiment.
Figure 3B:
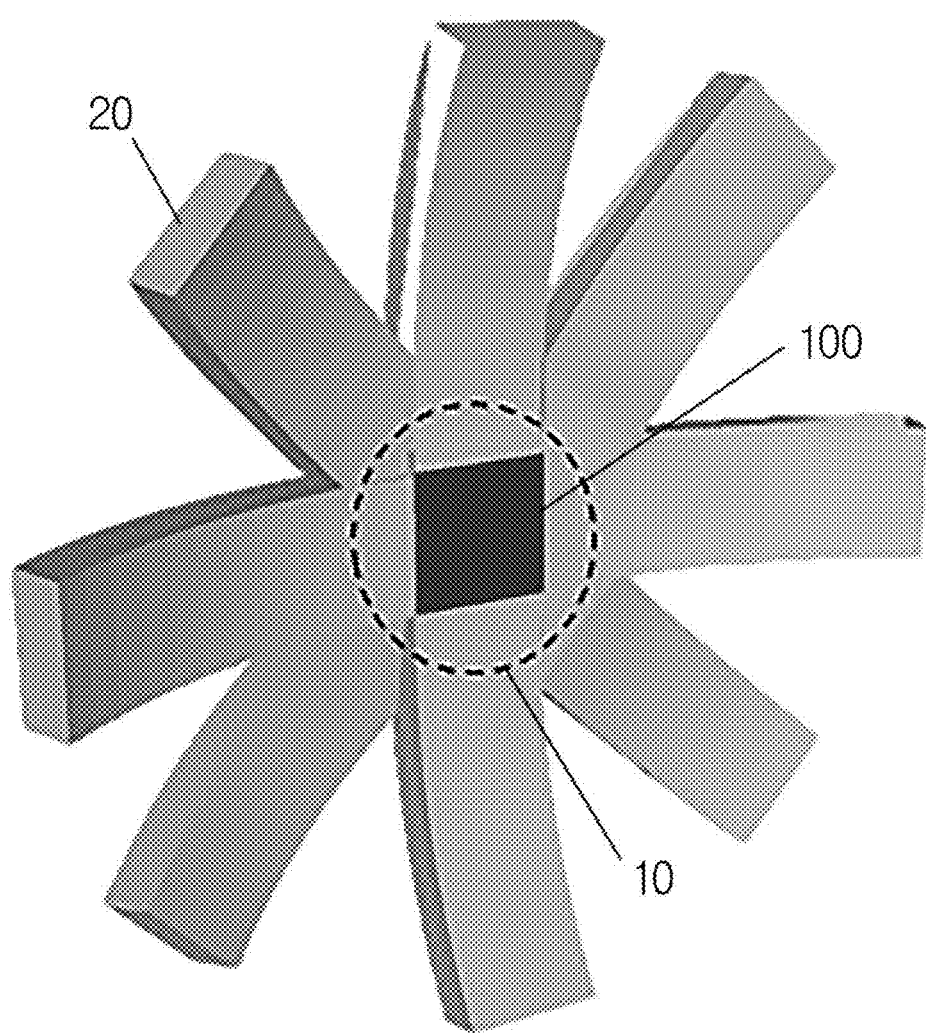

FIGS. 3A and 3B show the structure of the flexible ultrasound transducer according to another embodiment.

Referring to FIG. 3A, the ultrasound probe 100 disposed at the central part 10 of the substrate may have a 2D array structure in which the plurality of imaging ultrasound output elements is arranged in a circular shape. In this case, as opposed to the 1D array structure of FIGS. 1 and 2, it is possible to acquire a 2D image of the region of interest without rotation of the ultrasound probe.

Referring to FIG. 3B, the ultrasound probe 100 disposed at the central part 10 of the substrate may have a 2D array structure in which the plurality of imaging ultrasound output elements is arranged in a square shape. Also in this case, in the same way as the structure of FIG. 3A, the 2D image of the region of interest may be acquired.

Figure 4:
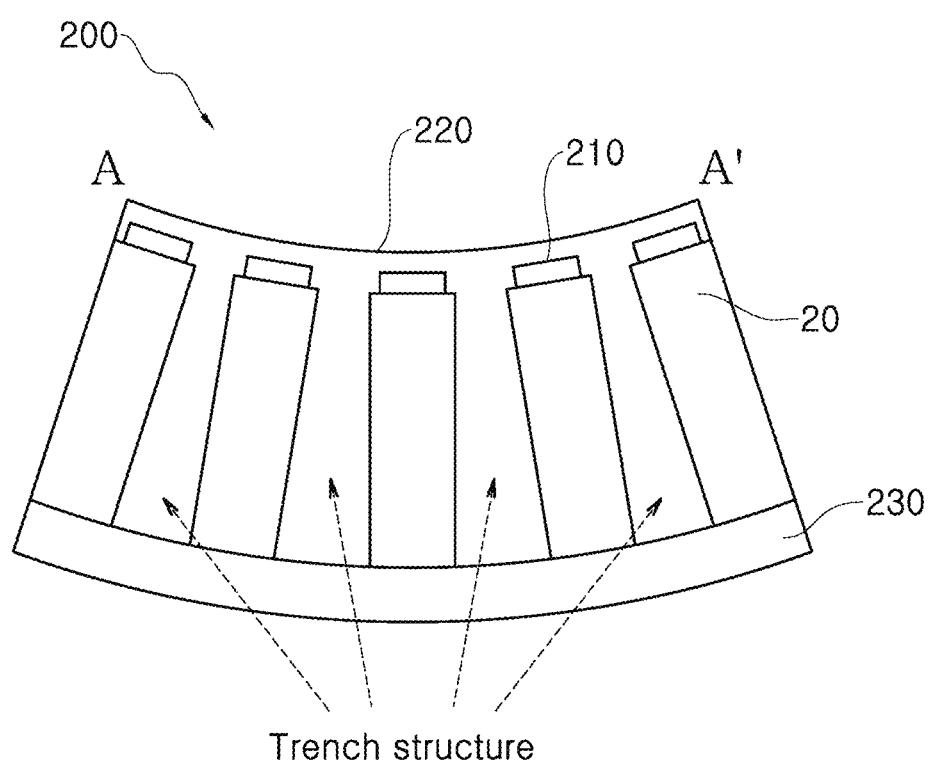
FIG. 4 shows a cross section of a focused ultrasound output unit disposed at an extended part of a substrate of a flexible ultrasound transducer according to an embodiment.

FIG. 4 shows a cross section of the focused ultrasound output unit disposed at the extended part of the substrate of the flexible ultrasound transducer according to an embodiment. FIG. 4 is a cross-sectional view of part of the focused ultrasound output unit 200 disposed at the extended part 20 of the substrate in FIG. 1, taken along the dashed line A-A.

Referring to FIG. 4, the extended part 20 of the substrate has a plurality of trench structures formed at a predetermined interval. The trench structure is filled with a flexible material, for example, elastomer including at least one of polydimethylsiloxane (PDMS), polyurethane, polyester or a mixture thereof in the transducer production process, and a resulting flexible material layer 220 covers the trench structures and the array of focused ultrasound output elements 210.

According to an embodiment, the focused ultrasound output unit 200 may further include a reinforcing layer 230 made of a material having a larger thermal expansion coefficient than the flexible material layer 220 below the extended part 20 of the substrate, Through this, it is possible to control the curvature of the element substrate and reinforce the substrate.

Accordingly, the extended part 20 of the substrate and the focused ultrasound output unit 200 have a flexible structure and are prone to deform by the external pressure or recover. The curvature or elasticity of the substrate may vary depending on the detailed design variables such as the type and amount of materials of each layer, and the heating temperature in the production process.

As shown in FIG. 4, the focused ultrasound output elements 210 are arranged on the extended part 20 of the substrate at a predetermined interval. Each focused ultrasound output element 210 is an element that converts the alternating current energy to mechanical vibration of the same frequency to produce an ultrasound, and may be a micromachined ultrasound transducer such as, for example, capacitive micromachined ultrasound transducer (CMUT) or piezoelectric micromachined ultrasound transducer (PMUT). The focused ultrasound output elements 210 may output Low-intensity Focused Ultrasound (LIFU) for stimulating the region of interest with low intensity, or High-intensity Focused Ultrasound (HIFU) for mechanically removing the lesion in the region of interest, by adjusting the output according to a target area to treat and the goal of treatment. The output ultrasound may overlap to form an ultrasound beam, and may achieve therapeutic effect in the human body tissue.

According to an embodiment, HIFU has the intensity sufficient to apply thermal or mechanical stimulation to the detected lesion such as tumor to mechanically remove the lesion. For example, HIFU has the center frequency of 1 MHz or higher and the intensity of 3 W/cm$^2$ (Ispta) or higher. In contrast, LIFU has the frequency enough to penetrate the skull, and a proper intensity to mechanically stimulate the human body tissue without damaging it. For example, LIFU has the center frequency of about 200 kHz to 1 MHz and the intensity of 3 W/cm$^2$ (Ispta) or less.

The user may arbitrarily control the detailed settings such as frequency, intensity, thermal/mechanical stimulation type change of the ultrasound outputted from the focused ultrasound output unit 200, through a control device and an interface connected to the ultrasound transducer element.

Figure 5A:
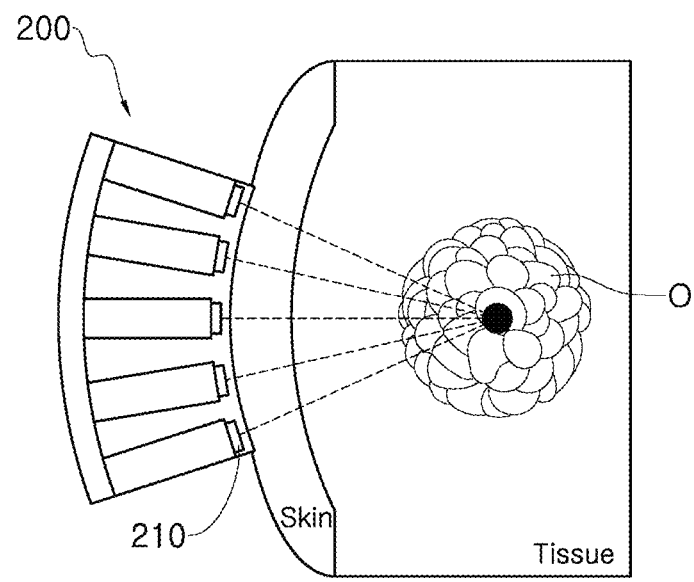
FIGS. 5A and 5B show the focal position adjustment through flexible movement of an extended part of a substrate of a flexible ultrasound transducer according to an embodiment.
Figure 5B:
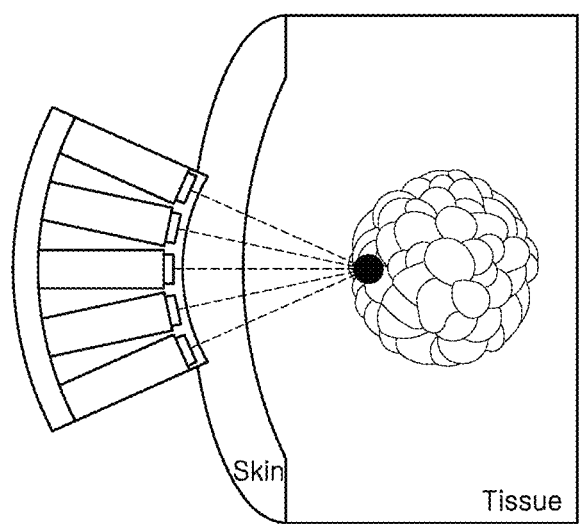

FIGS. 5A and 5B show the focal length (focal position) adjustment through flexible movement of the flexible ultrasound transducer according to an embodiment.

As shown in FIG. 5A, as the focused ultrasound output unit 200 disposed at the extended part of the substrate has a flexible property, the focused ultrasound output unit 200 comes into close contact with the skin along the curved shape of the skin. As shown in FIG. 5A, each focused ultrasound output element 210 outputs a high intensity or low intensity ultrasound beam, and the ultrasound beam converging to the focal point in the region of interest removes or stimulates the object O, for example, a tumor, a cancer cell, a lesion and a living tissue. As the focused ultrasound output unit 200 has a flexible property, the user may adjust the focal length of the focused ultrasound by arbitrarily bending the substrate. For example, as shown in FIG. 5B, when the curve of the substrate is larger, the focal point to which the ultrasound beam converges is closer.

The existing ultrasound transducer (having a stiff substrate) needs to change the focal position by controlling the location or phase of each transducer of the transducer array. According to an embodiment of the present disclosure, it is possible to adjust the focal length as desired or bring the ultrasound output unit into close contact with the skin along the skin curve changes through flexible movement of the substrate.

Hereinafter, a method for manufacturing the flexible ultrasound transducer according to an embodiment will be described with reference to FIGS. 6A to 6F.

Figure 6A:
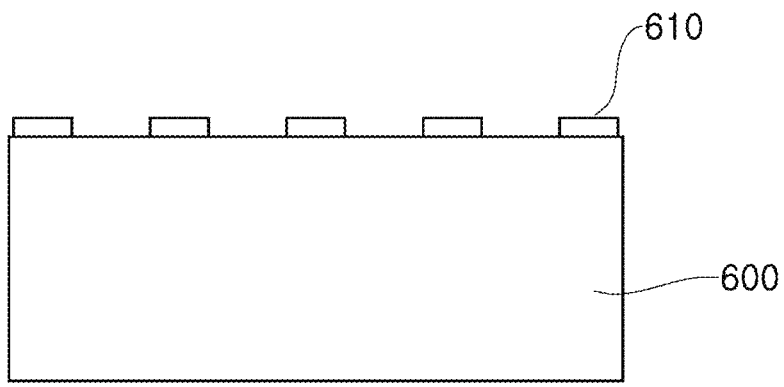
FIGS. 6A to 6F show the process of a method for manufacturing a flexible ultrasound transducer according to an embodiment.

First, as shown in FIG. 6A, the step of arranging a plurality of focused ultrasound output elements 610 on a provided substrate 600 at a predetermined interval is performed. The substrate 600 may be made of a mixture of silicon and a material that is different from silicon, but is not limited thereto. The ultrasound output element 610 may be a micromachined ultrasound transducer such as CMUT or PMUT, and may output LIFU (for example, ultrasound having the center frequency of 200 kHz to 1 MHz and the intensity of 3 W/cm$^2$ (Ispta) or less) for stimulating the region of interest with low intensity, or HIFU (ultrasound having the center frequency of 1 MHz or higher and the intensity of 3 W/cm$^2$ (Ispta) or higher) for mechanically removing the lesion in the region of interest, according to a target area to treat and the goal of treatment.

Figure 6B:
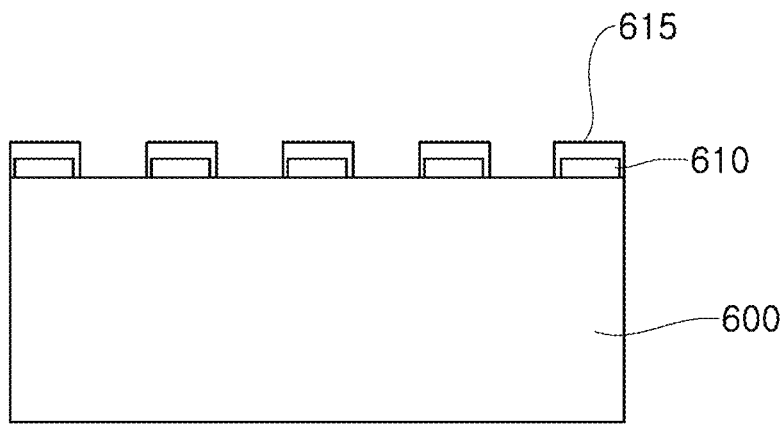

Subsequently, as shown in FIG. 6B, the step of forming a photoresist 615 on each focused ultrasound output element 610 is performed. The photoresist refers to photosensitive resin that solidifies when exposed by an exposure device. The photoresist 615 includes components that do not decompose by an etching solution and protects the focused ultrasound output elements 610 and the underlying substrate 600 to prevent them from being etched in the subsequent process.

Figure 6C:
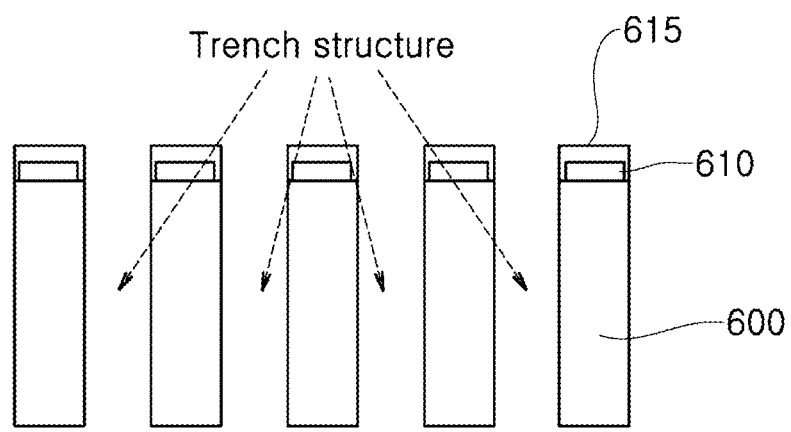

Subsequently, as shown in FIG. 6C, the step of forming a plurality of thin trench structures between the plurality of focused ultrasound output elements 610 by etching the substrate 600 is performed. According to an embodiment, wet etching using a chemical solution that can react with the silicon substrate or dry etching using ionized gas may be used.

Figure 6D:
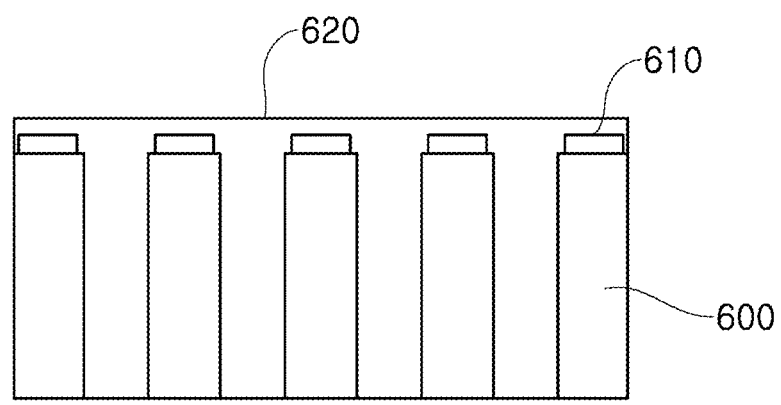

Subsequently, as shown in FIG. 6D, the step of removing the photoresist 615, and then forming a flexible material layer 620 that covers the trench structures and the focused ultrasound output elements 610 is performed. For example, the flexible material layer 620 is made of elastomer including at least one of polydimethylsiloxane (PDMS), polyurethane, polyester or a mixture thereof. When the flexible material fills the trench structures of the substrate 600, the substrate can make a flexible movement.

Figure 6E:
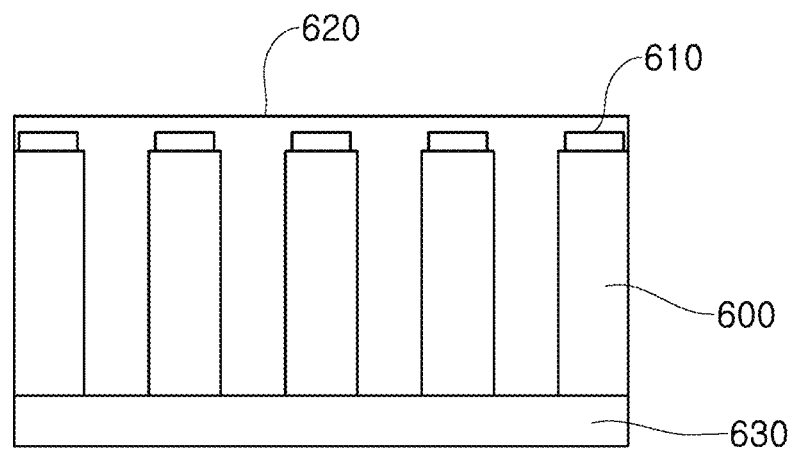

According to an embodiment, as shown in FIG. 6E, the step of forming a reinforcing layer 630 made of a material having a larger thermal expansion coefficient than the flexible material layer 620 below the substrate 600; and the step of applying heat to the flexible material layer 620 and the reinforcing layer 630 may be further performed. The reinforcing layer 630 may be made of a material, for example, parylene (plastic obtained by para-xylene polymerization), having a larger thermal expansion coefficient than PDMS used to form the flexible material layer 620.

Figure 6F:
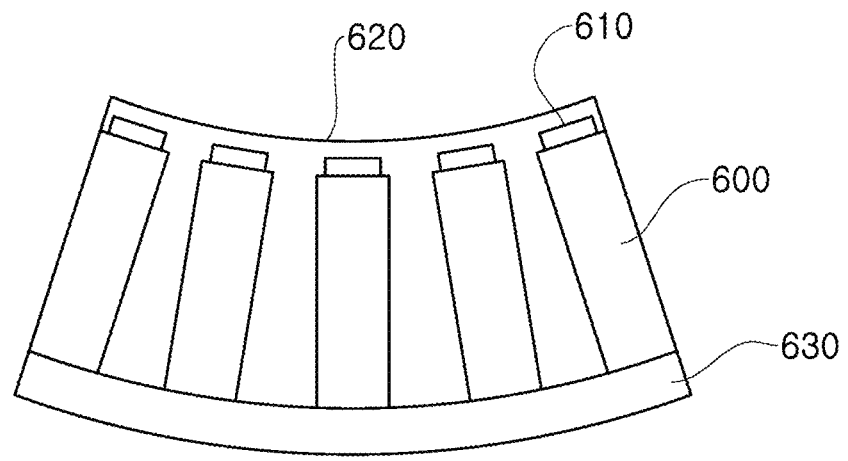

Accordingly, due to the higher rate of increase of volume of the reinforcing layer 630 having a larger thermal expansion coefficient than the flexible material layer 620, the curvature of the element may increase. As shown in FIG. 6F, the substrate is bent toward the surface opposite the surface on which the reinforcing layer 630 is formed. The curvature or elasticity of the substrate may vary depending on the type and amount of materials of the flexible material layer 620 and/or the reinforcing layer 630 and the extent of heating in the production process.

Figure 7:
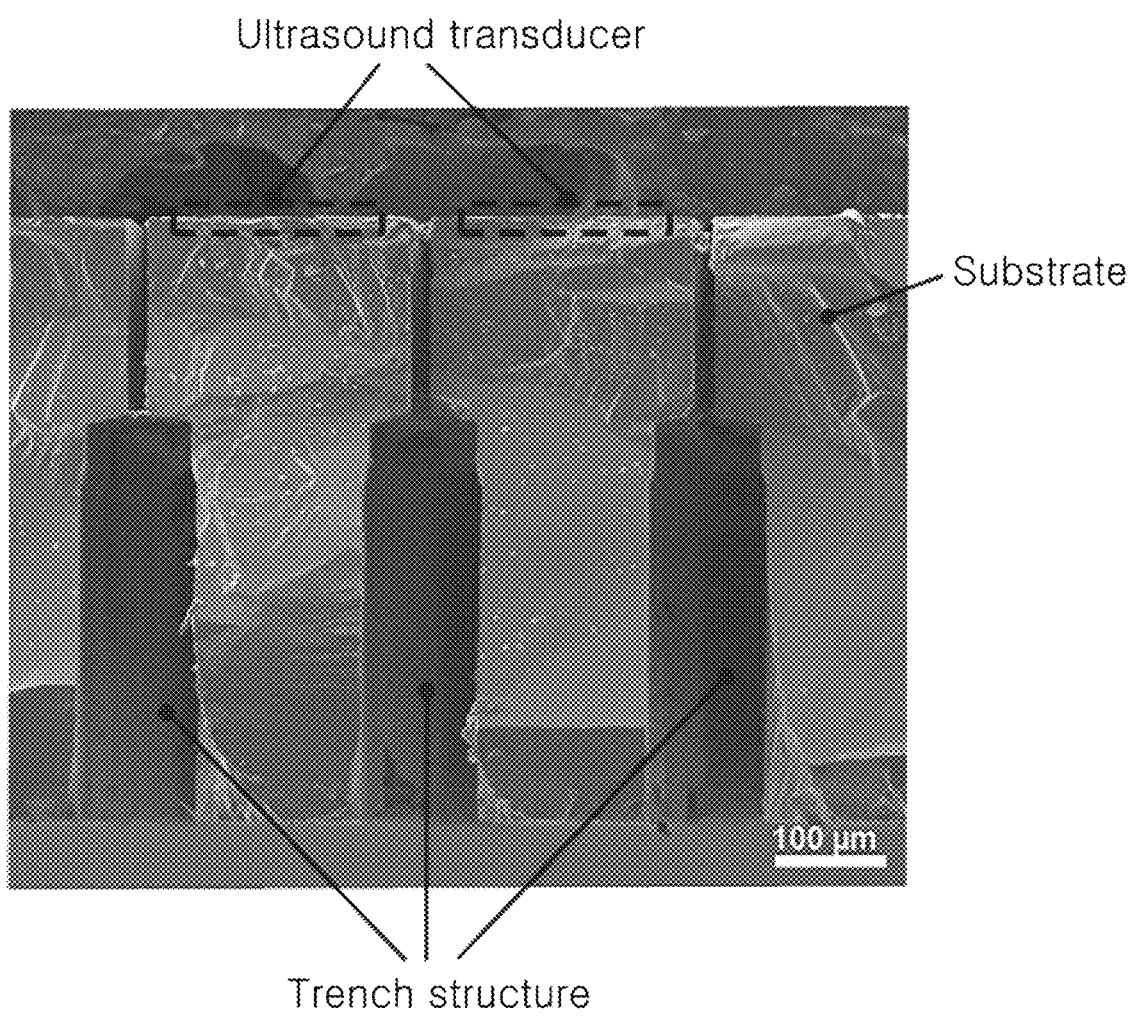
FIG. 7 shows an electron microscope image of a cross-sectional structure of a flexible ultrasound transducer according to an embodiment.

FIG. 7 is an electron microscope image of the cross-sectional structure of the flexible ultrasound transducer according to an embodiment. As shown, the flexible ultrasound transducer element may be manufactured by arranging ultrasound transducer elements on the substrate, forming trench structures between the ultrasound transducer elements and filling the trench structures with the flexible material, so that the flexible ultrasound transducer element may come into close contact with the skin or change the focal position through flexible movement.

According to the above-described embodiments, there is provided a dual mode ultrasound transducer that can simultaneously achieve ultrasound image acquisition at the central part through the ultrasound probe, and ultrasonic therapy (lesion stimulation or removal) at the flexible extended part using focused ultrasound while being in close contact with the skin.

The existing dual mode ultrasound transducer uses a process of individually fabricating a high frequency output unit for ultrasound imaging and a low frequency output unit for ultrasonic therapy and combining them, and thus has increased cost, high volume and heavy weight disadvantages. According to the present disclosure, it is possible to design with different response characteristics of frequency necessary for treatment and frequency necessary for imaging by differently arranging the transducer elements on each part (the central part and the extended part) of the substrate without needing to assemble the transducer. Accordingly, it is possible to reduce the production cost and the volume and weight of the element.

Additionally, attempts have been made to solve the process complexity issue by uniformly arranging CMUT elements, but according to an embodiment of the present disclosure, a 1D array of CMUTs and a 2D array of CMUTs are each arranged on each part of the substrate, thereby solving the process complexity issue and maximizing the role of the ultrasound transducer.

To adjust the focal length, a mechanical connection device has been required, which allows the tilting movement of the transducer array through independent time delays, but according to an embodiment of the present disclosure, it is possible to further improve the focal sensitivity necessary for ultrasound imaging and treatment through flexible movement of the flexible substrate of the transducer element itself.

Thus, it is possible to directly control a focal point of a desired target area using the CMUT sensor by adding the flexible material layer to the existing substrate without requiring any driving unit to move the focal point of focused ultrasound. Accordingly, it is possible to maximize the function of the transducer without the addition of other components.

While the present disclosure has been hereinabove described with reference to the embodiments, it will be apparent to those having ordinary skill in the corresponding technical field that various modifications and changes may be made to the present disclosure without departing from the spirit and scope of the present disclosure set forth in the appended claims.

What is claimed is:

1. A flexible ultrasound transducer, comprising:
   a substrate having a central part and a plurality of extended parts extending from the central part;
   an ultrasound probe disposed at the central part of the substrate to acquire an ultrasound image of a region of interest, wherein the ultrasound probe includes a circular array of imaging ultrasound output elements configured to output an imaging ultrasound toward the region of interest; and
   a plurality of focused ultrasound output units disposed at the plurality of extended parts of the substrate to output a focused ultrasound to the region of interest, wherein the focused ultrasound output units include an array of focused ultrasound output elements, a plurality of trench structures each of which is formed between the focused ultrasound output elements, and a flexible material disposed in the plurality of trench structures and that covers the plurality of trench structures and the array of focused ultrasound output elements,
   wherein each of the plurality of extended parts includes a reinforcing layer disposed on an opposing side of the substrate from the plurality of focused ultrasound output units, the reinforcing layer being a material having a larger thermal expansion coefficient than the flexible material;
   wherein the extended parts of the substrate and the focused ultrasound output units are flexible and deformable.

2. The flexible ultrasound transducer according to claim 1, wherein the array of focused ultrasound output elements are configured to output a focused ultrasound for treatment to the region of interest.

3. The flexible ultrasound transducer according to claim 2, wherein the focused ultrasound for treatment is Low-intensity Focused Ultrasound for stimulating the region of interest with low intensity or High-intensity Focused Ultrasound for removing a lesion in the region of interest.

4. The flexible ultrasound transducer according to claim 1, wherein the ultrasound probe or the focused ultrasound output units include an ultrasound output element which is a micromachined ultrasound transducer (MUT).

* * * * *